(12) United States Patent
Baldwin

(10) Patent No.: US 8,783,263 B2
(45) Date of Patent: Jul. 22, 2014

(54) DECONSTRICTING AIRWAY DEVICES

(76) Inventor: Charles C. Baldwin, Columbia, MO (US)

( * ) Notice: Subject to any disclaimer, the term of this patent is extended or adjusted under 35 U.S.C. 154(b) by 125 days.

(21) Appl. No.: 13/506,247

(22) Filed: Apr. 6, 2012

(65) Prior Publication Data

US 2012/0199140 A1    Aug. 9, 2012

Related U.S. Application Data

(63) Continuation-in-part of application No. 12/316,793, filed on Dec. 17, 2008, now abandoned.

(51) Int. Cl.
*A61F 5/56* (2006.01)
*A61C 5/14* (2006.01)

(52) U.S. Cl.
USPC .......................... 128/859; 128/848; 128/861

(58) Field of Classification Search
USPC ................... 128/848, 859, 861, 862; 433/6
See application file for complete search history.

(56) References Cited

U.S. PATENT DOCUMENTS

| | | |
|---|---|---|
| 2,521,039 A | 9/1950 | Carpenter |
| 3,217,708 A | 11/1965 | Roberts |
| 5,427,117 A | 6/1995 | Thornton |
| 5,499,633 A | 3/1996 | Fenton |
| 5,941,246 A | 8/1999 | Roopchand |
| 6,830,051 B1 | 12/2004 | Lesniak et al. |
| 2008/0149110 A1 | 6/2008 | Baldwin |
| 2008/0149114 A1 | 6/2008 | Baldwin |
| 2008/0153056 A1 | 6/2008 | Baldwin |
| 2008/0153057 A1 | 6/2008 | Baldwin |

OTHER PUBLICATIONS

Miller's Anesthesia, 6th Edition, 2005, editor Ronald D. Miller, MD; Publisher Elsevier Churchill Livingston, Phi-PA, Chapt. 42, Airway Management, author: Thomas J.Gal, MD, pp. 1617-1652.
Clinical Anesthesia, 5th Edition, 2006; editors-Paul G. Brash, MD, Bruce F.Cullen, MD, Robert K. Stoetling, MD; Chapt.22, Airway Management, author William H. Rosenblatt, MD, pp. 595-642.
Monitored Anesthesia Care, 5th edition, 2006, Chapter 47, Simon H. Hiller, MD, and Michael S. Mazurek, MD, Clinical Anesthesia, 5th Edition, 2006, Chapter 47, pp. 1246-1261.

*Primary Examiner* — Patricia Bianco
*Assistant Examiner* — Keri J Nelson
(74) *Attorney, Agent, or Firm* — Paul M. Denk

(57) ABSTRACT

An intraoral airway having opposing trays with a soft lining or cushion to grip the maxillary and mandibular dental arches of a patient with a fixed relationship in such a manner as to gently open the mouth and thrust the mandibular component slightly forward thereby opening the oral cavity and hypopharynx for air/gas passage that is easily tolerated by fully awake patients/users as well as by sedated, anesthetized or obtunded patients.

3 Claims, 6 Drawing Sheets

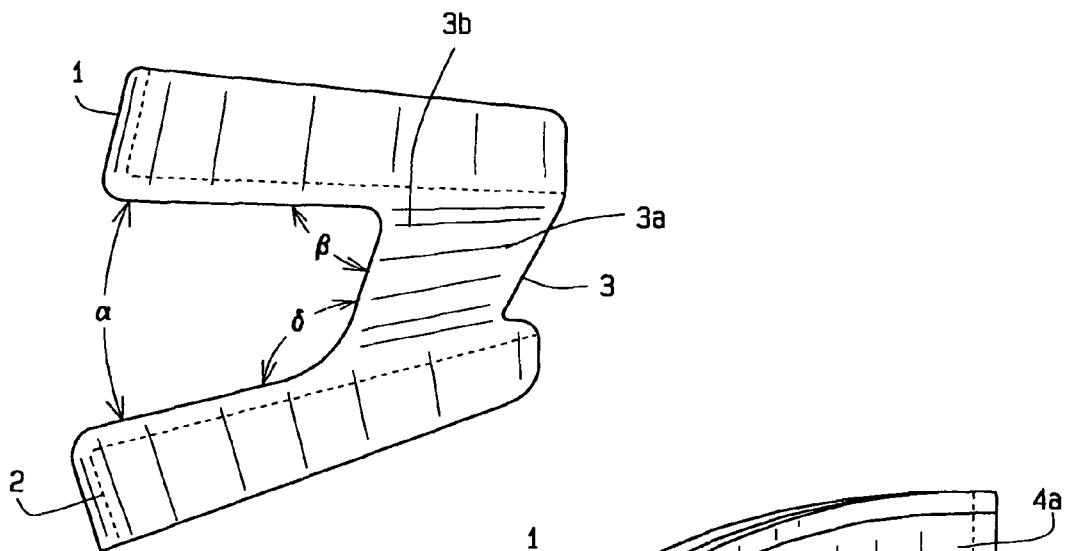
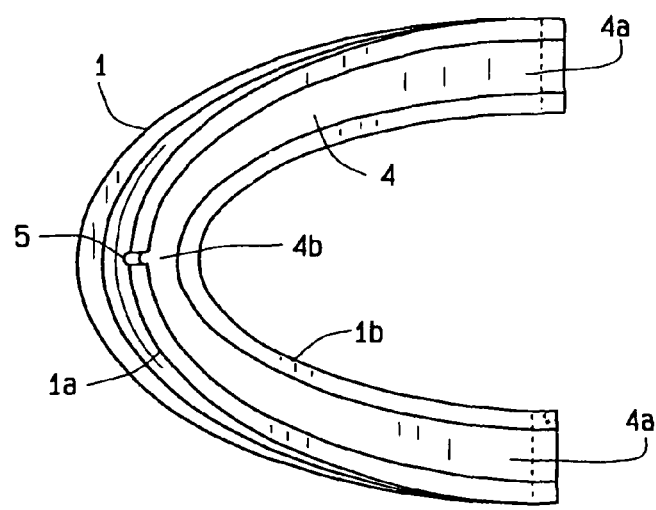
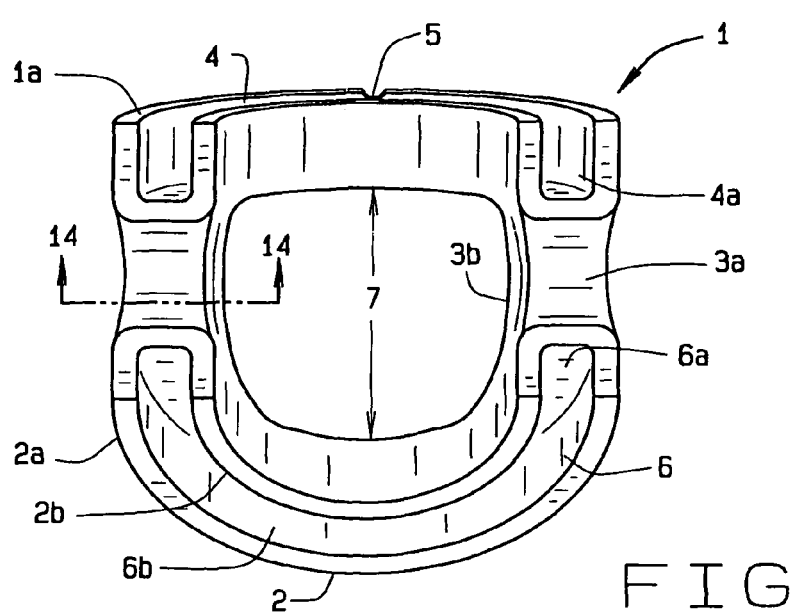
FIG. 1
FIG. 2
FIG. 3

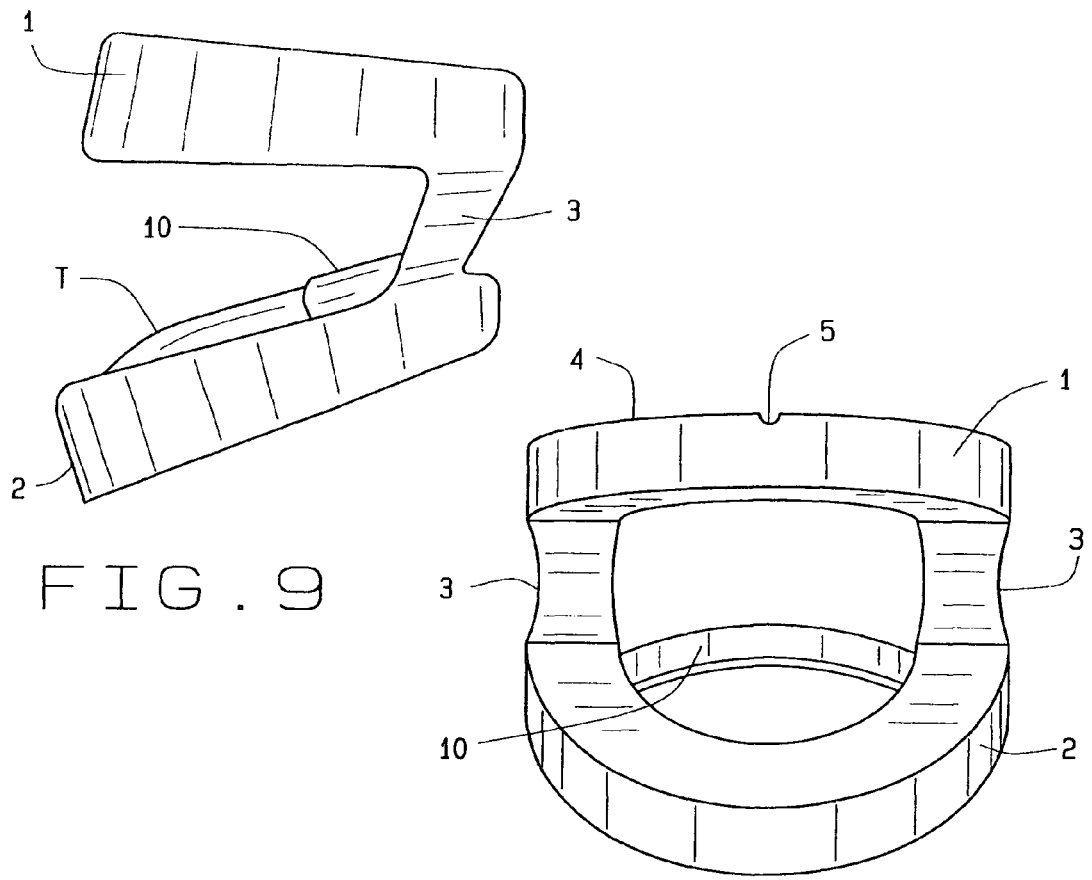
FIG. 9
FIG. 10
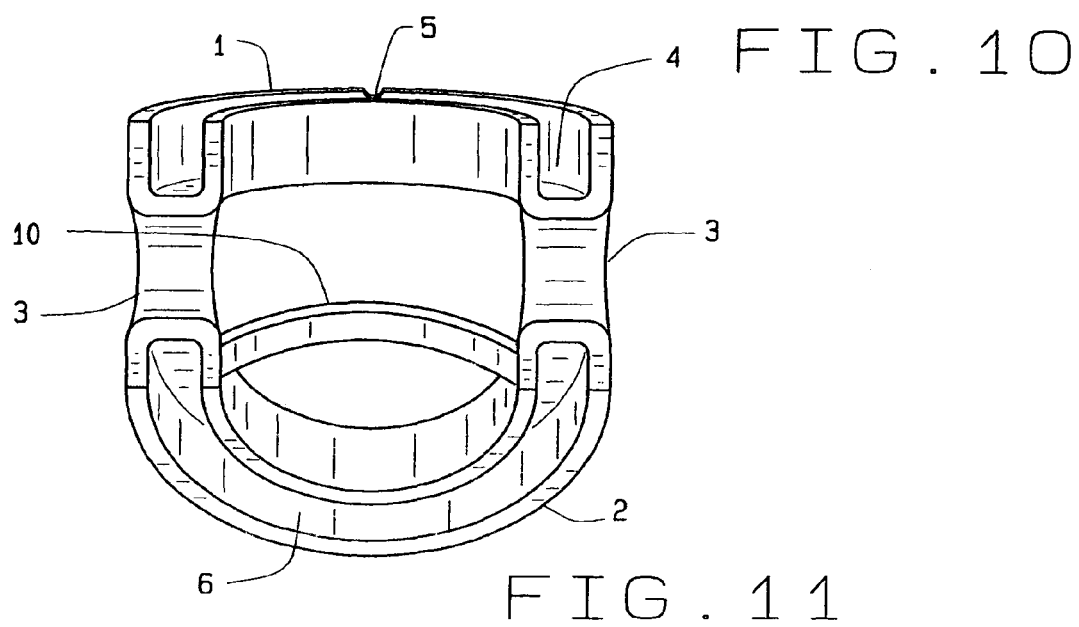
FIG. 11

DECONSTRICTING AIRWAY DEVICES

CROSS REFERENCE TO RELATED APPLICATIONS

This continuation application claims priority to the continuation in part application having Ser. No. 12/316,793, filed Dec. 17, 2008 now abandoned, the co-pending non-provisional application having a U.S. Ser. No. 11/602,918, filed Dec. 22, 2006, having Publication No. US 2008-0149110 A1, the co-pending non-provisional application having U.S. Ser. No. 11/602,919, filed Dec. 22, 2006, having Publication No. US 2008-0153056 A1, the co-pending non-provisional application having U.S. Ser. No. 11/602,920, filed Dec. 22, 2006, having Publication No. US 2008-0153057 A1, the co-pending non-provisional application having U.S. Ser. No. 11/602,921, filed Dec. 22, 2006, having Publication No. US 2008-0149114 A1, and the co-pending design patent application having U.S. Ser. No. 29/269,141 filed Dec. 12, 2006, and all of the aforesaid applications are commonly owned by the same inventor.

BACKGROUND OF THE INVENTION

The deconstricting airway devices generally relate to respiratory equipment and more specifically to a device that spreads the jaws of a patient to open the patient's airway for a medical procedure.

A core skill required in the practice of Anesthesia, Critical Care and Emergency Medicine and increasingly in other specialties such as cardiology that involve invasive procedures in which varying levels of sedation are given to patients is the maintenance of an open airway for spontaneously breathing patients and a patent passage for gases (e.g. oxygen) to allow ventilation in the obtunded and apneic patient. There are a myriad of airway devices to support these skills, all by creating a physical passageway to the hypopharynx and tracheal opening or through the trachea. None of these devices are tolerated by an awake or moderately sedated patient because they touch areas of the oro-naso and hypopharynx that elicit a powerful gagging and coughing reaction.

The patent human airway in which there is adequate and life supporting flow of gas to the lungs depends on the anatomy of the soft tissues of the tongue, palate and pharynx, the bones and joints of the face, and importantly the tone of the muscles embedded and animating these structures. As a person becomes somnolent, sedated or obtunded, tone decreases, the soft tissues collapse, and the mandible drops backward resulting in airway obstruction causing inadequate or no air movement even if the patient is still adequately breathing, with possible hypoxia leading, untreated, to death. This occurs even in sleep and can be pathologic with health consequences in Obstructive Sleep Apnea associated very strongly with obesity. Difficulty maintaining the airway even with very mild levels of sedation is also associated with obesity. Patients who are being anesthetized or deeply sedated will pass through a stage of light sedation both when being sedated and when awakening. This state is dangerous and difficult for the patient won't tolerate any standard airways but can obstruct anyway, and this difficulty is dramatically exacerbated by obesity, a condition increasingly common and associated with health needs, resulting in the likelihood of needing medical procedures or surgery.

Skilled airway managers such as anesthesiologists and anesthetists learn maneuvers to allow an air/gas passage to be maintained in the obtunded patient. Beside head and neck positioning, these chin lift and jaw thrust maneuvers take advantage of the unique anatomy of the human temporomandibular joint, a true double joint, a rotating ball joint until fully open, then becoming a cam joint as the mandibular condyle slides forward onto a bony shelf in the anterior portion of the joint, dropping the posterior part of the mandible, stretching the soft tissues and creating an air passage. In the airway maneuvers the mouth is not opened but by pulling the chin (in the patient not breathing) or pushing the angle of the jaw (in the breathing patient) the cam joint action is engaged, the hypopharynx is opened and a patent gas passage from the nose though the pharynx is created.

In American Medicine the number of invasive and uncomfortable procedures has been dramatically increasing, often to replace more invasive or surgical procedures that required general anesthesia. These procedures require some level of sedation so they can be tolerated by the patient, and in most institutions anything requiring more than a mild sedative that should not result in airway obstruction is attended by an anesthesia provider because of the consequences of even the slightest slip up in managing the airway. With aging and greater obesity even mild sedation can be dangerous. A device tolerated by an awake patient that would help maintain an open air passage as they are sedated or anesthetized and conversely could be left in the mouth as they awakened, would enhance the safety of sedation, and make many procedures more acceptable with less risk. Such a device may be used by a monitoring clinician other than an anesthesia provider not unlike the bite block used in endoscopy procedures which this device could replace, making not only a passage for the endoscope but helping maintain the airway. Such procedures may be less costly and more convenient to schedule if an anesthesia provider's attendance is not mandatory. And such a device might be useful in the management of Obstructive Sleep Apnea.

SUMMARY OF THE INVENTION

Generally, the present invention is an easily placed oral device with a soft lining to grip the dental, or alveolar, aches firmly to hold a fixed relationship of a slight angulation between the jaw and the roof of the mouth with a solid connection at the molar end of the arches to gently advance the mandible forward from the maxilla. The invention thus maintains an open air passage to the hypopharynx without touching any part of the mouth but the dental arches and the anterior tongue. The present invention has two arcuate trays upon gently bent connector pillars or buttresses forming a recognizable shape. The buttresses maintain the distance between the two trays.

The present invention has an anterior opening/aperture so it can be placed over objects already in the mouth or objects can be placed though it, such as a suction device to clear secretions. Instruments, such as bronchoscopes, endoscopes, or esophagogastroscopes, may be used within the airway. It can function as a bite block to protect such airways as an endotracheal tube or a larygneal airway. The invention can be placed over an already present endotracheal tube and then left in place until a patient is fully awake such as during emergence and recovery from a general anesthetic. The arches and connecting pillars should be made of a strong material that promotes comfort and is inert in the mouth. It can be used with any oxygen delivery device placed on the face and will be a useful adjunct to mask ventilating the patient during the induction of anesthesia or should the need arise in other circumstances. The airway should be available to in two versions to accommodate teeth or dentures and the edentulous state and still function as well.

The invention's design and appropriate sizes allows for use easily, even in emergent circumstances. Because the invention only grips the dental arches, of the mandible and the maxilla, it will not bother or irritate the mouth, oral structures, or pharyngeal structures, or stimulate strong reflexes such as gagging. An alternate embodiment incorporates a firm arch across the two legs of the mandibular component, but the anterior two thirds of the tongue, while quite sensitive to even light touch does not elicit strong reflexes. The firm grip on the dental arches makes the invention an anchor for other oral devices by firmly affixing them to it with a tie.

The present invention is an oral device designed to fit on the dental arches or alveolar ridges of both the maxilla and the mandible of a patient with connecting buttresses, or pillars. The pillars maintain an angular opening between the two arches thus establishing an open oropharynx. The present invention is suitable for use in the conscious, or awake, patient. The present invention incorporates a jaw thrust feature where the mandible of a patient is moved a few millimeters, approximately one to approximately three, frontally or anteriorly. The present invention utilizes the human temporomandibular joint's unique transition from a roller hinge joint to a cam joint which further opens the oropharynx but not increasing the angle of the patient's mouth further. The present invention has embodiments suitable for those patients with teeth or dentures and those patients without teeth, such as infants and the elderly, often called edentulous.

For most of its range of motion, the human temporo-mandibular joint opens upon a single point similar to a hinge. Approaching full opening, the mandibular condyle slides forward over the cartilaginous meniscus of the joint thus riding up a bony prominence like a cam. This cam opening of the joint further opens the posterior portion of the oropharynx, and in a sense slightly dislocating the jaw. Anesthesiologists and other health care providers take advantage of this anatomy. The providers push the mandible frontally, without opening the mouth, by placing their thumbs or fingers behind the angle of the mandible and gently thrusting forward, a maneuver called the jaw thrust.

The present invention emulates this maneuver by gently and firmly holding the dental ridges and teeth and slightly pushing the mandibular component forward in relation to the maxillary component. This maneuver has not been seen in existing airways found by the Applicant. Combined with partially opening the mouth and its non-gagging design, the present invention may be used in the fully awake patient who then may sleep or be sedated with the invention in place. Further, the present invention could be in place with the patient's level of consciousness altered and left in place as the patient awakens and returns to a fully awake state. The present invention can be used in the sedated, anesthetized, or obtunded patient. Unlike existing airway devices, such as the oropharyngeal or nasopharyngeal airways, the present invention can be placed at the beginning of a procedure when the patient is awake. The invention can then be left in the patient until the end of the procedure when the patient awakens and becomes fully aroused. However, the jaw thrust feature need not have the mouth opened to be effective because in the clinical, or manual, maneuver it usually results in a competent airway passage via the nasopharynx.

The present invention can also be used in the obtunded patient. An alternate embodiment of the invention includes an anchoring device, such as a zip or Nye tie, that secures another airway device, such as an endotracheal tube or a laryngeal mask airway, to the invention. The present invention stabilizes the movable components of the human airway and jaws, such as the mandible. By securing another airway device to the invention as during usage with a ventilated patient, the present invention provides a more secure attachment of the other airway device to itself than taping the other airway device to the patient's face. The ability of the present invention to secure another airway device has particular utility with the edentulous patients, in whom an endotracheal tube taped to the lip has a great deal of movement which may adversely affect patient ventilation.

The present invention also excludes the ability to stimulate, which is to induce the gagging reflex, of an awake patient. This exclusion maintains a patent upper airway even as a patient becomes somnolent, sedated, or anesthetized. The present invention falls below the tolerance of a fully awake user with intact cranial nerve reflexes. The angle between the upper and lower trays of the invention is generally below 20° but still as wide as possible for maximum benefit, least airway obstruction, to the patient.

The present invention further has a preferred embodiment for patients having teeth or dentures and at least one alternate embodiment for an edentulous, or toothless, patient. The alternate embodiment has a slightly taller and wider foam lining within the trays of the invention. The taller and wider lining holds the invention upon the gums and maintains the same height between the maxillary and mandibular components as the embodiment for the toothed patient.

The present invention, an oral device, has two arches, or trays, that gently hold both the maxillary and mandibular dental arches of a patient in a fixed position angled slightly open but not stimulating any part of the oropharynx thus allowing an awake patient to tolerate the invention. The invention has trays made of a resilient material, such as a soft plastic, and a foam insert to hold the teeth or edentulous arches. The trays conform to the shape of the teeth or edentulous arches along with the maxillary and mandibular anatomy. The trays are spaced apart by buttresses, also called pillars or columns. The present invention can be placed in the mouth by an awake patient. By gently maintaining the mouth slightly open, the invention enhances the patency of the airway. The jaw thrust feature of the invention capitalizes on the unique anatomy of the human temporo-mandibular joint wherein anterior (frontal) movement of only a few millimeters change the joint from a hinge to a cam. The hinge motion and cam motion of that joint remain separate and thus thrusting the mandibular component a few millimeters elevates the mandibular condyle which opens the oropharynx without gagging the patient, all the while enhancing airway patency. The invention can be used as a clinical airway in awake to sedated to anesthetized patients and in obtunded patients. The invention can be tolerated by more patients until a patient attains a fully awake state. Further, the patient may emplace the invention either for a medical procedure or as an airway support for mitigating OSA.

There has thus been outlined, rather broadly, the more important features of the invention in order that the detailed description thereof that follows may be better understood and that the present contribution to the art may be better appreciated. The present invention also includes sockets for the bale spears and for the back stops. Additional features of the invention will be described hereinafter and which will form the subject matter of the claims attached.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

The primary purpose of the invention is to maintain an open air or gas passage via the mouth and oropharynx by opening the mouth and advancing the mandible anteriorly while being tolerated by an awake patient.

Another object of the invention is that it be a single piece for quick placement as often required in acutely managing the human airway.

Another object of the invention is that it needs no adjustments to fit a patient and that it comes in a range of sizes to fit all patients.

Another object of the invention is that it be comfortable and not irritate the patient by gently fitting over the dental arches and maintaining a fixed angle and displacement between the upper (maxillary) and lower (mandibular) jaws, such that the patients can place and remove the invention in their own mouths.

Another object of the invention is that it does not trigger the gagging reflex, such as by touching any part of the oral cavity and oropharynx, so it would not cause untoward airway reactions in the lightly sedated or anesthetized patient while also maintaining a patent airway. The present invention fits comfortably and can be used in a fully awake person.

Yet another object of the invention is that it allows other devices, such as is suction tube or an endotracheal tube, to pass through an opening, and an alternate embodiment of the invention has a means to secure other devices to the airway for a more stable attachment than with tape and other adhesives.

Still another object of the invention is that the invention can be used in an operating room or procedure suite as a clinical airway support device in sedating or anesthetizing patients for medical procedures, including surgery, particularly when an endotracheal tube or pharyngeal airway passes through the invention but the invention must secure the tube against movement.

Still another object of the invention is that the invention manages the airway of a critically ill patient and those patients with respiratory failure and with ventilatory failure.

Still another object of the invention, in the embodiment with a cross piece that restrains the anterior tongue, is to accommodate patients with large tongues and low oral volumes often the obese patient.

Still another object of the invention is that it fits over the dental arches or alveolar ridges of an edentulous patient thus maintaining an open oral cavity with a large opening for air passage and optional passage of endoscopic device or other airways.

Still another object of the invention is that it gently holds the teeth or alveolar ridges for advancing the mandibular jaw approximately 5 to 20 millimeters thus creating a jaw thrust maneuver that maintains the patient's airway open.

Still another object of the invention is that it can be made in various sizes to fit children and adults and in various arrangements to adjust the amount of mandibular jaw advancement.

Still another object of the invention is that it functions as an airway splint in a fully awake patient for endoscopic examination with and without sedation.

Still another object of the invention is that it can be used in patients undergoing deep sedation and generally anesthesia because the patients will tolerate the invention from awakening to the end of the fully awake state. This object arises from the transition period when a patient emerges from deep is sedation and general anesthesia and during the transition period a patient has a low tolerance for existing upper airway devices placed within the mouth.

Still another object of the invention is that it can be used as a splint for bruxism, or teeth grinding, even during sleep.

Still another object of the invention is that it can be used for patients with obstructive sleep apnea, "OSA", to maintain a patent upper airway in sleep alone or as an adjunct to continuous positive airway pressure, "CPAP", devices. OSA has been increasing because of higher obesity rates and aging of the population. Further, the OSA patients, who often have obesity or morbid obesity, have a partial airway obstruction when mildly sedated and thus a low tolerance for existing airway devices. In OSA therapy, the large size and open design of the present invention protects the patient against aspiration or airway obstruction. The present invention aids those patients with a degree of respiratory compromise but too awake to tolerate other invasive devices. The present invention when used with CPAP devices and non-rebreathing masks avoids intubation and ventilatory support while delivering high oxygen flows.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In referring to the drawings,

FIG. 1 is a left side view of the preferred embodiment of the invention;

FIG. 2 is a top view of the preferred embodiment of the invention;

FIG. 3 is a rear view of the preferred embodiment of the invention;

FIG. 9 is a left side view of an alternate embodiment of the invention with a strip connecting the two legs of the mandibular arch to help contain a patient's tongue;

FIG. 10 is a front view of the alternate embodiment of the invention in FIG. 9;

FIG. 11 is a rear view of the alternate embodiment of the invention in FIG. 9;

The same reference numerals refer to the same parts throughout the various figures.

DESCRIPTION OF THE PREFERRED EMBODIMENT

Figure 4:
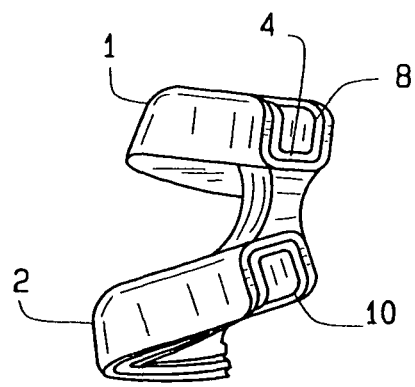
FIG. 4 is an oblique rear view of the left half of an embodiment of the invention showing the shape and height of the dental ridge trays and the material liners to accommodate patients with teeth or dentures.

The present invention overcomes the prior art limitations by providing a mouthpiece having two trays, each generally in an arch shape, one tray for each jaw of a patient. The trays are mutually spaced apart upon pillars locating at the ends of the trays. Beginning from the exterior of the invention, FIG. 1 provides a side view showing the maxillary tray 1 and mandibular tray 2 connected by a pillar 3 angled slightly anterior. The outside edge or lip 2b of the maxillary tray 2 is angled posteriorly from approximately 8° to approximately 18° as at angle α from vertical in relation to the floor of the tray to accommodate the slight anterior angulation of human upper incisors. Angle β between the maxillary tray and connecting pillar is less than 90 degrees and the angle γ between the mandibular tray and pillar is greater than 90 degrees. The mandibular tray protrudes anteriorly approximately 2-4 mm relative to the maxillary tray. The inner, or lingual, lip 1a, 2a of both trays is shorter than the outside, or buccal, lip 1b, 2b so it extends slightly up under the lips of a patient enhancing its secure position. The inner lip cooperates with the outside lip so the cross section of each tray conforms to the angle of the mucosa proximate the lingual edge of a patient's incisors. In the preferred embodiment, the outside lip and the inside lip of both trays have enough height to cover the incisors of a patient. In an alternate embodiment, the outside lips and the inside lips of both trays taper in height from a maximum near the molars to a minimum near the incisors of the patient. In an alternate embodiment, the inside lips of both trays taper at a greater rate than the outside lips of both trays which accommodates the flatter angle of the lingual mucosa.

The groove 4 of the maxillary tray 2 shown here in FIG. 2 and the groove 6 of the mandibular tray are lined with a soft foam material as later shown in FIGS. 4, 5, similar to a cushion or insert. A small U-shaped notch 5 is cut into the center of the outside, or buccal, lip 1a of the maxillary tray to accommodate the frenulum present in the mouth of most patients attached to the inner upper lip of a patient. The maxillary tray 1 has a generally arch like shape, to follow the teeth and gums, as seen from above. The maxillary tray 1 has two legs, as at 4a, spaced apart in the vicinity of the molars that join together at a peak, as at 4b, in the vicinity of the incisors. The mandibular tray 2 also has a generally arch like shape, to follow the teeth and gums, as later shown in FIG. 3. The mandibular tray 2 also has two legs, as at 6a, generally locating below those legs of the maxillary tray and joining at a peak, as at 6b. The device preferably has two pillars 3 extending between the legs of the mandibular tray and the maxillary tray, opposite the peaks of each tray. The pillars hold the mandibular tray 2 spaced below the maxillary tray 1 at least one centimeter and at a decline of angle 7, the decline is approximately 5° to approximately 20°, and preferably 15° beyond, or more than, a right angle, 90°, with the pillar. The spacing and angle between the two trays maintain the patient's mandibular arch open from the maxillary arch and allow for free passage of air or equipment through the patient's mouth.

An oval shaped aperture 7 is formed by the trays and the pillars connecting to them in FIG. 3. This aperture is approximately 2.5-3 cm high at the midline. The connecting pillars 3 are smooth, thick enough to resist the jaw muscles, and in cross section triangular shaped, narrow anteriorly as at 3b to accommodate the tongue for comfort and widen towards the throat of a patient as at 3a. The shapes of the maxillary tray and the manidbular tray, viewed in cross section as from the outside loop 1a to the inner loop 1b, are slightly parabolic, more so than U-shaped to fit the alveolar ridges of the human maxilla and mandible.

Figure 5:
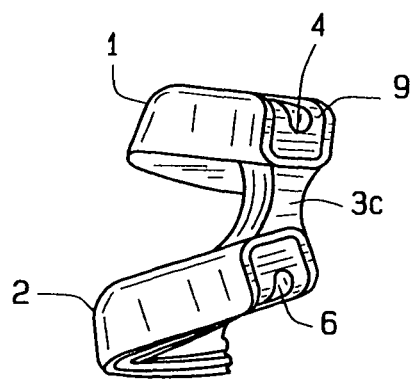
FIG. 5 is an oblique rear view of the left half of an embodiment of the invention showing the narrower shape, greater height, and narrower groove in the lining material to accommodate the edentulous patient and the invention is symmetric and the right half is a mirror image of this figure.

FIGS. 4, 5 show the rear views of the left half of the preferred and alternate embodiments of the invention respectively. The grooves 4, 6 in both trays 1, 2 and the lining material, or cushion, are slightly wider and higher in the version in FIG. 4 for a patient with teeth or dentures. For the toothed patient, a liner 8 has a deeper channel to admit the teeth but still reach the alveolar ridges, or gums. The grooves 4, 6 in both trays 1, 2 in FIG. 5 are narrower, more V shaped and the edges slightly shorter in FIG. 5 to fit the edentulous patient in whom the mucosa of the narrow alveolar ridges will sit directly in the soft lining material. For the patient without teeth, a liner 9 has a shallower channel than in the toothed version that reaches the alveolar ridges without need of accommodating the teeth. Because of the loss of vertical space due to the absence of teeth, the connecting pillar 3c in the edentulous version will be slightly taller than the connecting pillar 3 in the version for patients with teeth or dentures.

Figure 6:
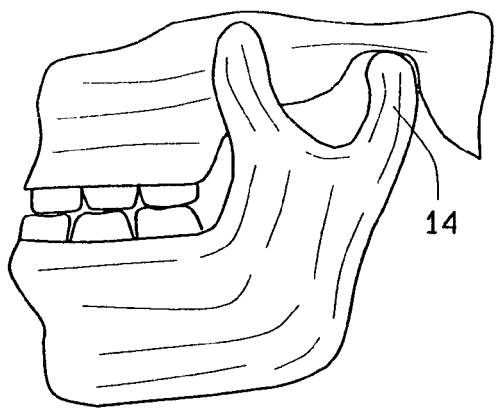
FIG. 6 is a schematic view of the normal left temporomandibular joint with the mouth closed and at rest.
Figure 7:
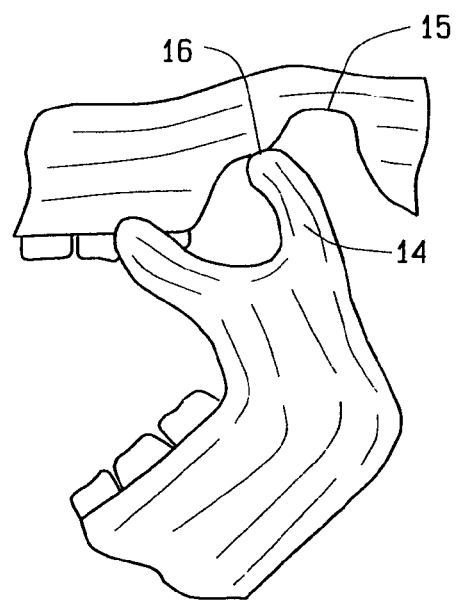
FIG. 7 is a schematic view of the normal left temporomandibular joint with the mouth fully opened.
Figure 8:
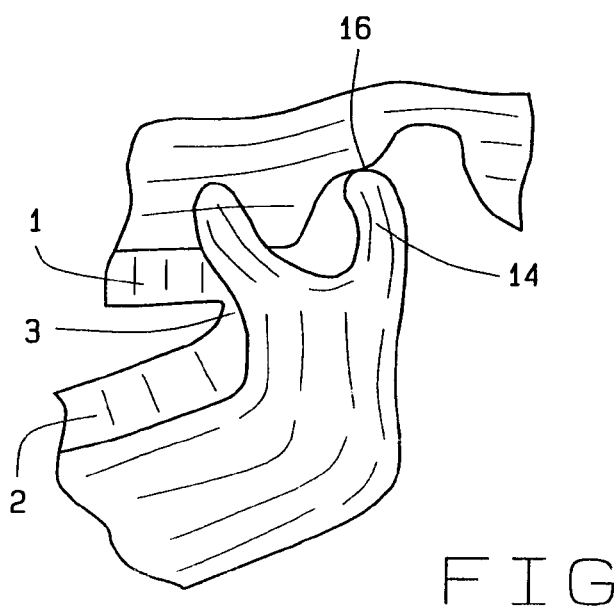
FIG. 8 is a schematic view of the normal left temporomandibular joint with the invention in place demonstrating its effect on the joint, mandibular position and mouth opening.

FIG. 6 demonstrates the human temporomandiular joint at rest with the mandibular condyle 14 in the rounded maxillary portion of the joint with the mouth closed. FIG. 7 shows when fully opened the condyle pivots as at 15 and then slides forward onto a bony ridge at the anterior portion of the maxillary part of the jaw. By riding onto this ridge 16 the mandible drops down and moves forward a small amount. Both motions stretch the soft tissues of the pharynx significantly, thus opening both the mouth and hypopharynx more than usual, allowing the mandible to advance approximately 5 to approximately 20 millimeters in reference to the maxilla. FIG. 8 demonstrates how the invention of dual trays 1, 2, snugly in place on the mandible and maxilla, opens the mouth by rotating the condyle and also by sliding the condyle on the bony ridge 16 dropping the mandible slightly and pulling it forward, exactly emulating the natural motion in FIG. 7 even though the mouth is only partially opened for comfort. This results in an optimally opened hypopharynx even when motor tone is lost as in sedation or obtundation.

FIG. 9 shows a side view, FIG. 10 shows a front view, and FIG. 11 shows a rear view of an alternate embodiment of the invention with an arch 16 crossing both legs of the mandibular tray 2, generally proximate the pillars. The arch is of the same material as the remainder of the invention and bridges the molar portions. The arch has a height in the direction of the maxillary tray of about 21 mm or less. In the preferred embodiment, the arch is integral with the mandibular tray and the maxillary tray and is generally located proximate the molars of the patient. This slightly compresses the anterior tongue, as at T, of the patient towards the floor of the mouth thus enhancing the invention's capacity to maintain a patent airway in patients with small mouths and/or large tongues without gagging, common among obese patients. This alternate embodiment gently holds down the tongue and holds it forward while contacting non-gag inducing portions of the tongue. This alternate embodiment may be employed in patients with large tongues or small mandibles. Awake patients may emplace the alternate embodiment within their mouths as they can move their tongues into a comfortable position for optimal airway opening.

The arch may be ovoid, or round in cross section for patient comfort. The arch may also taper in thickness towards center yet still hold tongue to floor of mouth. The arch locates rearwardly to provide anterior space for comfortable tongue placement by medical staff or an awake patient.

Figure 12:
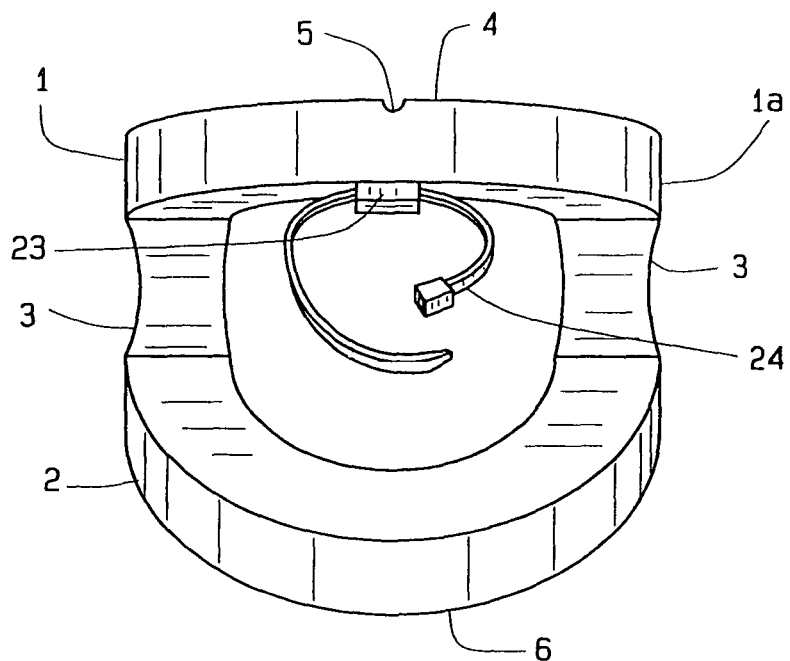
FIG. 12 is a front view of another alternate embodiment of the invention that incorporates a small square protrusion of material on the maxillary arch that receives a component, such as a ratcheted plastic tie, to secure other oral devices.
Figure 13:
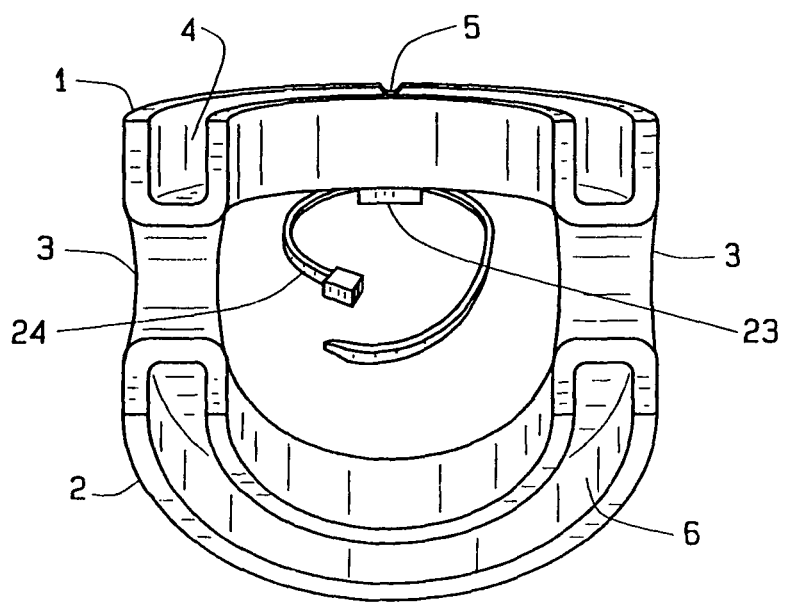
FIG. 13 is a rear view of another alternate embodiment of the invention as depicted in FIG. 12; and, FIG. 14 provides a cross-sectional view of the triangular pillar taken along the line 14-14 of FIG. 3.
Figure 14:
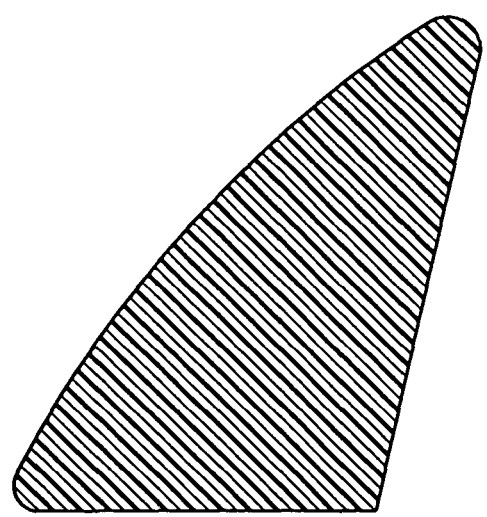

FIG. 12 provides a front view and FIG. 13 describes a rear view of another alternate embodiment of the invention respectively showing a cleat, such as a small integral rectangular block 23, on the inferior surface of the midline of the maxillary tray 2 perforated to accommodate a means of fixing 24 an endotracheal tube or other devices to the airway. Such fixing means include a nylon tie as depicted in the figure however; the Applicant foresees other grasping means to secure devices to the invention such as straps hook and loop fasteners, sutures, threads, and knotted loops. It needs to be affixed to the maxillary tray to stabilize the tube in relation to the structures of the head and neck since the jaw (mandible) can move.

From the aforementioned description, deconstricting airway devices have been described. The deconstricting airway devices are uniquely capable of advancing the lower jaw ahead of the upper jaw of a patient in a jaw thrust maneuver that maintains an open airway. The present invention can be installed and removed by a conscious patient or readily installed and removed by medical staff for a sedated patient. The present invention has various sizes to fit patients. This device assembles two trays, one for each jaw with or without teeth, where the trays are supported upon pillars so that the jaws maintain an open airway for the patient. The device and its various components may be manufactured from many materials, including but not limited to, such as the trays of a soft toxic plastic and a soft pliable cushion or insert for placement or lining within the tray of polymers, ABS plastic, polyvinyl chloride, polyethylene, polypropylene, select metals, their alloys, and composites.

As such, those skilled in the art will appreciate that the conception, upon which this disclosure is based, may readily be utilized as a basis for the designing of other structures, methods and systems for carrying out the several purposes of the present invention. Therefore, the claims include such equivalent constructions insofar as they do not depart from the spirit and the scope of the present invention.

I claim:

1. A deconstricting airway device for emplacement in the mouth of a patient, comprising:
   an arch shaped tray adapted to grasp the maxilla of the patient and forming a maxillary tray, said tray having two legs joining at a peak;
   said maxillary tray further comprising a resilient and durable material having a groove with a generally U shaped cross-section including an outside lip and a spaced apart inside lip connecting by a floor;
   a cushion locating within said groove of said maxillary tray;
   another arch shaped tray adapted to grasp the mandible of the patient and forming a mandibular tray;
   said mandibular tray further comprising a resilient and durable material having a groove with a generally U shaped cross-section including an outside lip and a spaced apart inside lip connecting by a floor;
   another cushion inserting within said groove of said mandibular tray;
   at least two pillars being nonflexible and integrating with said trays and extending approximately vertically between said leg of one tray and said leg of another tray;
   at approximate their back edges thereof, said pillars being spaced apart and located at the rear of each tray, the non-flexibility of said pillars preventing the maxillary tray and mandibular tray from movement towards each other, and to maintain the distance between said trays during usage of the deconstricting airway device;
   said mandibular tray adapting to cover the mandibular dental arch of the patient and said maxillary tray adapting to cover the maxillary dental arch of the patient;
   said outside lip and said inside lip of each tray attaining an orientation of approximately 8° to approximately 18° posterior from the vertical;
   said mandibular tray having sufficient height to cover the incisors of the patient;
   said maxillary tray having sufficient height to cover the incisors of the patient;
   said outside lip and said inside lip of each tray having an angle from the base of the support approach back to vertical as it is molded toward the molar teeth;
   said maxillary tray attaining an included angle with said pillars of less than 90°;
   said mandibular tray attaining an included angle with said pillars of more than 90°;
   said inside lip of each of said trays being shorter than said outside lip of each of said trays wherein said inside lip and said outside lip are adapted to conform to the angle of the mucosa arising from the lingual edge of the incisors of the patient;
   said inside lip of each of said maxillary tray and said mandibular tray tapering in height at a greater rate than said outside lip thus accommodating the flatter angle of the lingual mucosa of the patient;
   said pillars extending from said maxillary tray to said mandibular tray and holding said mandibular tray spaced below said maxillary tray wherein said mandibular tray attains an orientation angled downwardly away from said maxillary tray;
   said pillars locating coplanar with said outside lip of both trays thus minimizing abrasions to the mouth of the patient;
   said maxillary tray and said mandibular tray adapting to maintain the mandibular arch of the patient open from the maxillary arch of the patient in the mouth of the patient;
   said pillars spacing said maxillary tray and said mandibular tray at least one centimeter apart;
   said pillars orienting said mandibular tray at approximately a 5° to approximately 20° below said maxillary tray;
   said mandibular tray adapting to advance the mandibular arch of the patient forward to engage the camming features of the patient's temporo-mandibular joint particularly positioning the mandibular condyle over the meniscus of the temporo-mandibular joint of the patient;
   said mandibular tray adapted to retain opened the oropharynx of the patient and maintain patency of the patient's airway;
   said maxillary tray and said mandibular tray each being narrow at the peak of said tray and widening away from the peak of the tray along the legs of the tray attaining maximum width proximate said pillars;
   said device gently grasps the maxilla and the mandible of the patient while avoiding contact with any structures of the patient capable of triggering a gag reflex in the patient;
   an integral cleat locating below said maxillary tray proximate the peak, said cleat capable of receiving a tying device, such as a zip tie;

said outside lip of said maxillary tray having a notch centered therein proximate said peak, said notch adapting to admit the frenulum of the patient;

said mandibular tray including an integral arch spanning between the legs proximate to said pillars and adapting to span between the premolar portions of a patient's mandibular arch;

said integral arch having a cross section that avoids triggering the gag reflex of the patient;

said integral arch having a slight height towards said maxillary tray of less than about 21 mm wherein said integral arch gently retains the patient's tongue upon the floor of the patient's mouth;

said arch has a thickness tapering from proximate the legs to the peak;

wherein said integral arch locates generally rearward of said pillars thus providing anterior space for comfortable tongue placement;

said cushions are generally foam material having a thickness of a U shaped cross section including with an outside lip and an inside lip joined by a floor, said outside lip and said inside lip cooperating with said thickness, and said outside lip and said inside lip and floor having a height to hold the teeth of a patient and said foam material fits within each tray; and said cushions are generally foam material having a thickness and a U shaped cross section including with an outside lip and an inside lip joined by a floor, said outside lip and said inside lip cooperating with the thickness to hold the alveolar ridges of an edentulous patient.

2. A mouthpiece emplaced in the mouth of a patient and functions as a deconstricting airway device that maintains the patient's airway open and allows passage of air and equipment there through, comprising:

an arch shaped tray adapted to grasp the maxilla of the patient and form a maxillary tray, said maxillary tray having two legs joining at a peak, said maxillary tray being of a resilient and durable material and having a generally U shaped groove including an outside lip and a spaced apart inside lip connected by a floor;

another arch shaped tray adapted to grasp the mandible of the patient and forming a mandibular tray, said another tray having two legs joining at a peak, said mandibular tray being of a resilient and durable material having a U shaped groove including an outside lip and a spaced apart inside lip connecting by a floor;

at least two pillars being nonflexible and integrating with each of said trays and extending vertically between said leg of one tray and said leg of another tray, said pillars being spaced apart and located at the rear of each tray, the non-flexibility of said pillars preventing the maxillary tray and mandibular tray from movement towards each other, and to maintain the distance between said trays during usage of the said mouthpiece;

said mouthpiece advancing said mandibular tray downwardly and forwardly of said maxillary tray and adapting to move the mandible forward of the maxilla of a patient thus maintaining the patient's airway open;

said outside lip and said inside lip of each tray having an angle from the base of the support approach back to vertical as it is molded towards the molar teeth;

said maxillary tray attaining an included angle with said pillars of less than 90°;

said mandibular tray attaining an included angle with said pillars of more than 90°;

said pillars spacing said maxillary tray and said mandibular tray at least 1 centimeter apart;

said pillars orienting said mandibular tray and approximately 5° to approximately 20° below said maxillary tray;

said mandibular tray adapting to advance the mandibular arch of the patient forwardly and to engage the camming features of the patient's temporo-mandibular joint particularly positioning the mandibular condyle over the meniscus of the temporo-mandibular joint of the patient; and, said mandibular tray adapted to open the oropharynx of a patient and maintain patency of the patient's airway.

3. The deconstricting airway device of claim 2 wherein said pillars having a cross-sectional triangular shape being narrower anteriorly, and widened towards the throat of the patient, to comfortably accommodate the tongue of the patient during usage of said device, said triangulated pillars being thick enough to resist distortion of the patient's jaw muscles during usage of said device.

* * * * *